US005773000A

United States Patent [19]
Bostwick et al.

[11] Patent Number: 5,773,000
[45] Date of Patent: Jun. 30, 1998

[54] THERAPEUTIC TREATMENT OF CLOSTRIDIUM DIFFICILE ASSOCIATED DISEASES

[75] Inventors: Eileen F. Bostwick, Dayton; Robert A. Hoerr, Long Lake, both of Minn.

[73] Assignee: GalaGen Inc., Arden Hills, Minn.

[21] Appl. No.: 730,437

[22] Filed: Oct. 15, 1996

Related U.S. Application Data

[63] Continuation of Ser. No. 300,918, Sep. 6, 1994, abandoned.
[51] Int. Cl.[6] .................. A61K 39/395; A61K 39/40; C07K 16/12
[52] U.S. Cl. ........................... 424/167.1; 424/150.1; 424/164.1; 424/130.1; 530/388.4; 530/389.5; 530/387.1
[58] Field of Search .................. 424/150.1, 164.1, 424/167.1; 530/388.4, 389.5, 387.1

[56] References Cited

U.S. PATENT DOCUMENTS

| | | | |
|---|---|---|---|
| 5,013,569 | 5/1991 | Rubin | 426/858 |
| 5,106,618 | 4/1992 | Beck et al. | 424/85.8 |
| 5,258,178 | 11/1993 | Cordle et al. | 424/85.8 |

FOREIGN PATENT DOCUMENTS

94/13264  6/1994  WIPO .

OTHER PUBLICATIONS

John G. Bartlett, *Antibiotic–Associated Diarrhea*, Clinical Infectious Disease 1992, 15:573–81.
Corthier et al., *Emergence in Gnotobiotic Mice of Nontoxinogenic Clones of clostridium difficile from a Toxinogenic One*, Infection and Immunity, Jun. 1988, pp. 1500–1504.
Corthier et al, *Protection Against Experimental Pseudomembranous Colitis in Gnotobiotic Mice by Use of Monoclonal Antibodies Against clostridium difficile Toxin A*, Infection and Immunity, Mar. 1991, pp. 1192–1195.
Dove et al., *Molecular Characterization of the clostridium difficile Toxin A Gene*, Infection and Immunity, Feb. 1990, pp. 480–488.
Ehrich et al., *Production of clostridium difficile Antitoxin*, Infection and Immunity, Jun. 1980, pp. 1041–1043.
Gerding et al, *clostridium difficile –Associated Diarrhea*, Archives of Internal Medicine, vol. 146, Jan. 1986, pp. 95–100.
Kelly et al., *clostridium difficile Colitis*, New England Journal of Medicine, vol. 330, Jan. 1994, pp. 257–262.
Kelly et al., *Human Colonic Aspirates Containing Immunoglobulin A Antibody to clostridium difficile Toxin A Inhibit Toxin A –Receptor Binding*, Gastroenterology, vol. 102, No. 1, pp. 35–40.
Lima et al, *Effects of clostridium difficile Toxins A and B in Rabbit Small and Large Intestine In Vivo and on Cultured Cells In Vitro*, Infection and Immunity, Mar. 1988, pp. 582–588.

Lyerly et al., *clostridium difficile: Its Disease and Toxins*, Clinical Microbiology Reviews, Jan. 1988, pp. 1–18.
Lyerly et al., *Characterization of Toxins A and B of clostridium difficile with Monoclonal Antibodies*, Infection and Immunity, Oct. 1986, pp. 70–76.
Lyerly et al., *Passive Immunization of Hamsters Against Disease Caused by clostridium difficile by Use of Bovine Immunoglobulin G Concentrate*, Infection and Immunity, Jun. 1991, pp. 2215–2218.
Mahe et al., *Effect of Various Diets on Toxin Production by Two Strains of clostridiumd difficile in Gnotobiotic Mice*, Infection and Immunity, Aug. 1987, pp. 1801–1805.
Martinez et al., *Purification and Characterization of clostridium sordellii Hemorrhagic Toxin and Cross–Reactivity with clostridium difficile Toxin A (Enterotoxin)*, Infection and Immunity, May 1988, pp. 12–15–1221.
McFarland et al., *Nosocomial Acquisition of clostridium difficile Infection*, The New England Journal of Medicine, Jan. 1989, pp. 204–210.
McFarland et al, *Review of clostridium difficile Associated Diseases*, American Journal of Infection Control, vol. 14, No. 3, Jun. 1986, pp. 99–104.
Mitchell et al., *Effect of Toxin A and B of clostridium difficile on Rabbit Ileum and Colon*, Gut., 1986, vol. 27, pp. 78–85.
Morris et al, *Role of Surgery in Antibiotic–Induced Pseudomembranous Enterocolitis*, The American Journal of Surgery, vol. 160, Nov. 1990, pp. 535–539.
Rothman et al., *Differential Cytotoxic Effects of Toxins A and B Isolated from clostridium difficile*, Infection and Immunity, Nov. 1984, pp. 324–331.
Triadafilopoulos et al., *Differential Effects of clostridium difficile Toxins A and B on Rabbit Ileum*, Gastroenterology, 1987, vol. 93, pp. 273–279.
Tucker et al., *Toxin A of clostridium difficile Is a Potent Cytotoxin*, Journal of Clinical Microbiology, May 1990, pp. 869–871.
Barroso et al., *Nucleotide Sequence of clostridium difficile Toxin B Gene*, Nucleic Acids Research, vol. 18, No. 13, p. 4004.
Lyerly et al., *Biological Activities of Toxins A and B of clostridium difficile*, Infection and Immunity, vol. 35, No. 3, Mar. 1982, pp. 1147–1150.
Lyerly et al., *Effects of clostridium difficile Toxins Given Intragastrically to Animals*, Infection and Immunity, vol. 47, No. 2, Feb. 1985, pp. 349–352.

(List continued on next page.)

*Primary Examiner*—Susan A. Loring
*Attorney, Agent, or Firm*—Merchant, Gould, Smith, Edell, Welter & Schmidt, P.A.

[57] ABSTRACT

The effective treatment of *Clostridium difficile* associated diseases, such as *Clostridium difficile* colitis, pseudomembranous colitis and antibiotic associated diarrhea, by administering an antibody having specific activity against *Clostridium difficile* colitis and toxins thereof alone or in combination with vancomycin, bacitracin or metronidazole is herein described as well as pharmaceutical compositions therefor.

6 Claims, 10 Drawing Sheets

OTHER PUBLICATIONS

Corthier et al., *Prevention of clostridium difficile Induced Morality in Gnotobiotic Mice by Saccharomyces boulardii*, Canadian Journal of Microbiology, vol. 32, No. 11, Nov. 1986, pp. 894–896.

Kimmey et al., *Prevention of Further Resources of clostridium difficile Colitis with Saccharomyces boulardii*, Digestive Diseases and Sciences, vol. 35, No. 7, Jul. 1990, pp. 897–901.

Surawicz et al., *Prevention of Antibiotic–Associated Diarrhea by Saccharomyces boulardii: A Prospective Study*, Gastroenterology, vol. 96, No. 4, Apr. 1989, pp. 981–988.

Toothaker et al, *Prevention of Clindamycin–Induced Mortality in Hamsters by Saccharomyces boulardii*, Antimicrobial Agents and Chemotherapy, vol. 26, No. 4, Oct. 1984, pp.552–556.

Fernie et al., *Active and Passive Immunization to Protect Against Antibiotic Associated Caecitis in Hamsters*, Developments in Biological Standardization, vol. 53, 1982, pp. 325–332.

Libby et al., *Effects of Two Toxins of clostridium difficile in Antibiotic–Associated Cecitis in Hamsters*, Infection and Immunity, vol. 36, No. 2, May 1982, pp. 822–829.

Boesman–Finkelstein et al., *Bovine Lactogenic Immunity Against Cholera Toxin–Related Enterotoxins and vibrio cholerae Outer Membranes*, Infection and Immunity, vol. 57, No. 4, Apr. 1989, pp. 1227–1234.

Brussow et al., *Bovine Milk Immunoglobulins for Passive Immunity to Infantile Rotavirus Gastroenteritis*, Journal of Clinical Microbiology, vol. 25, No. 6, Jun. 1987, pp. 982–986.

Fayer et al., *Immunotherapeutic Efficacy of Bovine Colostral Immunoglobulins from a Hyperimmunized Cow Against Cryptosporidiosis in Neonatal Mice*, Infection and Immunity, vol. 58, No. 9, Sep. 1990, pp. 2962–2965.

Hilpert et al., *Use of Bovine Milk Concentrate Containing Antibody to Rotavirus to Treat Rotavirus Gastroenteritis in Infants*, Journal of Infectious Diseases, vol. 156, No. 1, Jul. 1987, pp. 158–166.

Mietens et al., *Treatment of Infantile E. coli Gastroenteritis with Specific Bovine anti–E. coli Milk Immunoglobulins*, European Journal of Pediatrics, vol. 132, No. 4, 1979, pp. 239–252.

Tacket et al., *Protection by Milk Immunoglobulin Concentrate Against Oral Challenge with Enterotoxigenic Escherichia coli*, The New England Journal of Medicine, vol. 318, No. 19, May 1988, pp. 1240–1243.

Yoshiyama et al., *Specific Antibodies to cholera Toxin in Rabbit Milk are Protective Against vibrio cholerae–induced Intestinal Secretion*, Immunology, vol. 61, No. 4, Aug. 1987, pp. 543–547.

Pothoulakis et al, *Characterization of Rabbit Ileal Receptors for clostridium difficile Toxin A*, The Journal of Clinical Investigation, vol. 88, No. 1, Jul. 1991, pp. 119–125.

Leung et al., *Treatment with Intravenously Administered Gamma Globulin of Chronic Relapsing colitis Induced by clostridium difficile Toxin*, The Journal of Pediatrics, vol. 118, No. 4, Part 1, Apr. 1991, pp. 633–637.

Corthier et al., *Modulation of Cytotoxin Production by clostridium difficile in the Intestinal Tracts of Gnotobiotic Mice Inoculated with Various Human Intestinal Bacteria*, Applied and Enviromental Microbiology, vol. 49, No. 1, Jan. 1985, pp. 250–252.

Borriello et al., *Host and Microbial Determinants of the Spectrum of clostridium difficile mediated Gastrointestinal Disorders*, Microecolgy and Therapy, vol. 15, 1985, pp. 231–236.

Lucas et al., *Effect of Saccharomyces boulardii on Toxins Produced by clostridium difficile*, Microbial Ecology in Health and Disease, vol. 4, No. 4, 1991, p. 238.

Lancet The, vol. 341, 1993 London GB pp. 701–702, Tjellstrom Bo Et Al "Oral Immunoglobulin A Supplement in Treatment of clostridium difficile Enteritis".

Rothman S.W et al, Toxicon, 26 (6):583–597, 1988.

THERAPEUTIC TREATMENT OF CLOSTRIDIUM DIFFICILE ASSOCIATED DISEASES

This is a continuation of application Ser. No. 08/300,918, filed Sep. 6, 1994, now abandoned.

FIELD OF INVENTION

This invention relates to the treatment of *Clostridium difficile* associated diseases such as *Clostridium difficile* colitis, pseudomembranous colitis and antibiotic associated diarrhea by administration of specific antibodies in the form of oral and/or pharmaceutical compositions.

BACKGROUND OF THE INVENTION

*Clostridium difficile* was first described in 1935 as a gram-positive anaerobic bacillus. The bacterium was named "the difficult clostridium" because it resisted early attempts at isolation and grew very slowly in culture.

The bacterium became unnoticed until approximately the 1960's and 1970's where there occurred a rise in antibiotic associated pseudomembranous colitis due to wide usage of broad-spectrum antibiotic agents such as lincomycin and clindamycin. These antibiotics were found to cause diarrhea in approximately 10% of the patients and pseudomembranous colitis in approximately 1%. It is now clear that *C. difficile* is responsible for colitis in humans, antibiotic associated diarrhea and virtually all cases of pseudomembranous colitis.

The disease develops as a result of the production of two large toxins, toxin A ($M_r$, 308,000) and toxin B ($M_r$, 279,000), by the organism in the colon (Barroso, et al., *Nucleic Acids Res.*, 18:4004; Dove, et al., *Infect. Immun.*, 58:480–488; Lyerly, et al., *Clin. Microbiol. Rev.*, 1:1–18). Toxin A is believed to cause most of the gastrointestinal symptoms because of its enterotoxic activity in experimental animals (Borriello, et al., *Microecol. Ther.*, 15:213–236; Lyerly, et al., *Infect. Immun.*, 35:1147–1150; Lyerly, et al., *Infect. Immun.*, 47:349–352). There is some evidence suggesting that the toxins act synergistically during the course of the disease and that the initial tissue damage caused by toxin A allows toxin B to exert its toxic effect (Lyerly, et al., *Infect. Immun.*, 47:349–352).

Most patients with *C. difficile* disease are treated effectively with vancomycin, bacitracin, or metronidazole. Relapses occur in about 10–20% of the cases, however, indicating that antibiotic therapy is not always completely effective. As a result, research on alternative types of therapy is continuing. *Saccharomyces boulardii*, a yeast used to treat gastrointestinal illness, has shown promising results as a probiotic for the treatment of the disease in humans and in experimental animals (Corthier, et al., *Can. J. Microbiol.*, 32:894–896; Elmer, et al., *Antimicrob. Agents Chemother.*, 31:129–131; Kimmey, et al., *Dig. Dis. Sci.*, 35:897–901; Surawicz, et al., *Gastroenterology*, 96:981–988; Toothaker, et al., *Antimicrob. Agents Chemother.*, 26:552–556). The actual manner in which the yeast confers protection is unclear, although it has been reported that the yeast must be viable in order to provide protection (Lucas, et al., Presented at the 15th International Congress on Microbial Ecology of Disease, 7 to 9 Sep. 1990, Ioannina, Greece). Immunoprophylaxis has also been suggested as a type of treatment. It is known that vaccination against toxins A and B stimulates active immunity against *C. difficile* disease in experimental animals (Fernie, et al., *Dev. Biol. Stand.*, 53:325–332; Libby, et al., *Infect. Immun.*, 36:822–829). At the present time, however, suitable vaccines against the organism and its toxins have not been developed for individuals at high risk, and it is still unclear whether active immunization is appropriate. Alternatively, treatment by passive immunization has been suggested. In preliminary studies, serum antibodies against a toxigenic isolate of *C. difficile* protected hamsters against *C. difficile* disease when administered orally to the animals. Thus, passive immunity may be beneficial for prophylactic treatment.

Passive immunization with bovine antibodies has been examined as a possible alternative therapy in the treatment of other infectious diseases of the gastrointestinal tract, including diseases caused by rotavirus, enteropathogenic and enterotoxigenic *Escherichia coli*, *Vibrio cholerae*, and *Cryptosporidium parvum*, and the results indicate that antibodies administered in this manner provide protection (Boesman-Finkelstein, et al., *Infect. Immun.*, 57:1227–1234; Brussow, et al., *J. Clin. Microbiol.*, 25:982–986; Fayer, et al., *Infect. Immun.*, 58:2962–2965; Hilpert, et al., *J. Infect. Dis.*, 156:158–166; Mietens, et al., *Eur. J. Pediatr.*, 132:239–252; Tacket, et al., *N. Enql. J. Med.*, 318:1240–1243; Yoshiyama, et al., *Immunology*, 61:543–547). Passive immunity from bovine antibodies offers the advantages that most animals and humans tolerate the material given orally and that the predominant antibody species present, immunoglobulin G1 (IgG1), is relatively resistant to proteolysis.

A recent study reported on the ability of bovine immunoglobulin G(IgG) concentrate (BIC) from the colostrum of cows vaccinated with *C. difficile* toxoid to protect hamsters against experimental antibiotic associated cecitis. The results indicated that the hamsters were passively immunized against the disease if they were treated before the onset of diarrhea. The authors indicated that they were unable to effectively treat the hamsters with the hyperimmune BIC once they developed diarrhea (Lyerly, et al., *Infection and Immunity*, Vol. 59, No. 6, pages 2215–2218 (1991).

Thus, there is still a strong need for a method for effective treatment of antibiotic associated diarrhea, pseudomembranous colitis and *Clostridium difficile* colitis in humans without the fear of relapse in a significant amount of the patient population.

SUMMARY OF THE INVENTION

Accordingly the present invention includes a method of treating diseases associated with *C. difficile* colitis in a mammal, comprising: administering to said mammal an effective amount of an antibody having specific activity against *C. difficile* and toxins thereof found in the colon. Such diseases include, for example, *Clostridium difficile* colitis, pseudomembranous colitis, and antibiotic associated diarrhea.

A second aspect of the present invention is a pharmaceutical composition for use in treatment of diseases associated with *C. difficile* including, for example, pseudomembranous colitis or antibiotic associated diarrhea, in a patient, comprising: an effective amount of an antibody in combination with a pharmaceutically acceptable carrier adapted for oral or rectal administration, or enteric installation, the antibody having specific activity against *C. difficile* and toxins thereof.

A third aspect of the present invention is a pharmaceutical composition for use in treatment of pseudomembranous colitis or antibiotic associated diarrhea comprising: a combination of (a) an effective amount of an antibody having specific activity against *C. difficile* and toxins thereof, and (b) an effective amount of vancomycin, bacitracin, or metronidazole, in combination with a pharmaceutically acceptable carrier.

Finally, a fourth aspect of the present invention is a method of treating pseudomembranous colitis or antibiotic associated diarrhea in a patient comprising: administering to said patient an effective amount of an antibody having specific activity against *C. difficile* and toxins thereof concurrently or following the administration of an effective amount of vancomycin, bacitracin or metronidazole.

DETAILED DESCRIPTION OF THE INVENTION

Current therapies for *C. difficile*, antibiotic associated, diarrhea and colitis use antimicrobials such as metronidazole, bacitracin or vancomycin. These agents result in further disruption of the colonic flora and are associated with a 10–20% incidence of relapsing diarrhea.

The present invention provides an effective treatment which would not disturb the colonic flora. Anti-*C. difficile* bovine immunoglobulin concentrate (BIC) was prepared from the colostral milk of Holstein cows previously immunized with *C. difficile* toxoid (as described below in detail).

This concentrate contained high levels of bovine IgG specific for *C. difficile* toxins A and B as evaluated by ELISA. Anti-*C. difficile* BIC neutralized the cytotoxic effects of both *C. difficile* toxin A and B whereas control, non-immune, BIC did not. Anti-*C. difficile* BIC also inhibited the enterotoxic effects of *C. difficile* toxins on rat ileum as measured by increased rat ileal loop weight/length ratio (64% inhibition, $P<0.01$), increased mannitol permeability (89% inhibition, $P<0.01$) and histologic grading of enteritis ($P<0.01$ versus non-immune BIC). Thus, anti-*C. difficile* BIC neutralizes the cytotoxic effects of *C. difficile* toxins in vitro and inhibits their enterotoxic effects in vivo.

As a result of the above experiments, (described in greater detail in the examples) the inventors have discovered that administration of an immunoglobulin product containing specific antibodies to *C. difficile* results in the elimination of *C. difficile* toxins and also killing the bacteria within the colon and as such provides a realistic approach for effectively treating *C. difficile* associated diseases such as colitis, pseudomembranous colitis and antibiotic associated diarrhea and especially for patients experiencing multiple relapses.

For purposes of the present invention, the term "antibody having specific activity against *Clostridium difficile* and toxins thereof" is synonymous with "Anti-*C. difficile* bovine immunoglobin concentrate (BIC)".

The antibodies may be employed alone as a liquid or solid, preferably in a solid powder form and preferably in admixture with a carrier to form a pharmaceutical composition such as a tablet, capsule or suppository.

Since preferred methods of administration are oral and rectal, or enteric installation, and most preferred is oral, tablets and capsules are especially preferred, or enteric installation. These, of course, are prepared according to conventional methods known in the art. The antibodies may also be combined with other pharmaceutically acceptable carriers such as various liquids, proteins or oils which may also provide additional nutritional and/or pharmaceutical benefits.

Since the effect of the antibody is dependent on reaching the colon, preferred tablets or capsules should be enteric coated. Alternatively, the active antibodies can themselves be microencapsulated prior to formulation. Preparation of microcapsules of antibody as well as preparation of enteric coated tablets or capsules can be achieved by conventional methods known in the art.

Because the present antibodies first eliminate the *C. difficile* toxins, it is also advantageous to administer to patients suffering from *C. difficile* associated diseases a combination of the antibodies of the present invention with antibiotics prior known for treating pseudomembranous colitis and/or antibiotic associated diarrhea. Such antibiotics are for example vancomycin, bacitracin and metronidazole. Because of the speedy and quick elimination of the *C. difficile* toxins, the combination of antibody and antibiotic may be synergistic requiring much less antibiotic normally used in treating such diseases with results of decreased symptoms development, faster symptomatic relief and lower relapse rate. Recognized doses for administering metronidazole for example is 250 mg four times a day, and oral vancomycin is 125 mg four times a day. Administration of these antibiotics with the antibody of the present invention would result in use of substantially reduced dosage of antibiotics.

The administration of such a combination may be in a single dosage form where both active ingredients are combined and mixed with a pharmaceutically acceptable carrier. Preferred compositions would be those adapted for oral or rectal administration and it would include enteric coated tablets, capsules or suppositories.

The administration of the combination concurrently or following one another in separate dosage forms may still be formulated together in divided tablets or capsules. These are also known in the pharmaceutical art.

Treatment of patients suffering from *C. difficile* associated diseases with the combination of two active ingredients can take place not only concurrently in a single or separate dosage form but also following administration of one ingredient with the other. Preferably administration of the antibody followed by administration of the antibiotic would result in an effective treatment of the diseases.

The antibody of the present invention is contained in an immunoglobulin fraction provided to a patient. In such form, the amount of immunoglobulin provided to the patient is about 1 gram per day. Typically amounts from about 1 to 20 gram per day will be used. For example, about 1 to 2 grams of immunoglobulin could be given to a patient 3 to 4 time per day. The doses of the antibody formulation to be administered will depend upon the patient and the patient's medical history. Dosages of the specific antibody for adult humans envisioned by the present invention and considered to be therapeutically effective will range from between about 0.1 to 500 mg. However, it is to be understood that doses can readily be adjusted to provide appropriate amounts of the antibody to any patient, including children.

The invention is further described by reference to the following detailed examples, wherein the methodologies are as described below. These examples are not meant to limit the scope of the invention that has been set forth in the foregoing description. Variation within the concepts of the invention are apparent to those skilled in the art.

The disclosures of the cited references are incorporated by reference herein.

EXAMPLE 1

Antibody Production in Cows

Toxoid was prepared from *C. difficile* VPI 10463 culture filtrate, which contains high levels of toxin A and B. The strain was grown in brain heart infusion dialysis flasks at 37° C. for 72 h as previously described (Sullivan, et al., *Infect. Immun.*, 35:1032–1040) for the production of culture filtrate. The culture filtrate was subsequently converted to toxoid by adding 1/100 volume of formalin and incubating the mixture at 37° C. for 1 h. Analysis of the toxoid by tissue culture assay and mouse assay demonstrated that it retained <1% of its original cytotoxic and lethal activity. The challenge strain used in the animal model was *C. difficile* VPI 7698, which was isolated from a patient with pseudomembranous colitis and which produces intermediate levels of toxins A and B. Both bacterial strains were obtained from the anaerobe collection housed in the Department of Anaerobic Microbiology at Virginia Polytechnic Institute and State University (Blacksburg, Va.).

A total of 14 gestating Holstein cows were maintained according to generally accepted dairy management practices at the Land O'Lakes Answer Farm (Webster City, Iowa) or the research farm at Virginia Polytechnic Institute and State University. The cows were injected subcutaneously with 5 ml of toxoid (ca. 5 mg protein) emulsified in 5 ml of incomplete Freund adjuvant. Cows received multiple immunizations which began at least 60 days prior to the expected calving date. Test bleed samples were taken at the time of injection.

Colostrum was collected from the first six milkings of hyperimmunized cows and frozen within 2 to 3 h of collection. Colostrum was stored frozen until ready for processing. Briefly, the colostrum from all 14 cows was thawed, pooled and centrifuged to reduce the fat component.

The pH was lowered to precipitate the casein. The pH of the supernatant was then readjusted and the material was heat treated to reduce the bioburden. Ultrafiltration was used to reduce the lactose and mineral content. The material was heat treated again and spray dried to produce the bulk immunoglobulin concentrate as a shelf-stable powder. A nonimmune IgG concentrate from the colostrum of nonvaccinated cows was prepared in a similar fashion.

EXAMPLE 2

To confirm that immunization of cows with *C. difficile* antigens is associated with a subsequent increase in specific anti-*C. difficile* IgG in their colostral milk.
ELISA Method Bovine IgG levels to *C. difficile* were measured by ELISA using a modification of the method previously described (C. P. Kelly et al., *Gastroenterology* 1992; 102:35–40; D. Y. M. Leung et al., *J. Pediatr.* 1991; 118:633–637). Coating antigens used to measure IgG titers included purified *C. difficile* toxin A and purified *C. difficile* toxin.

Toxigenic *Clostridium difficile* was cultured for 72 hours in brain heart infusion broth (Beckton Dickinson, Cockeysville, Md.). The conditioned medium was centrifuged and the supernatant filter sterilized by passage through a 45 um filter (Nalgene). *C. difficile* toxins A and B were purified from the broth culture supernatant as previously described (C. Pothoulakis et al., *J. Clin. Invest.* 1991; 88:119–125). Microtiter plates (Immulon II, Dynatech) were coated with *C. difficile* toxin A or toxin B (each at 10 ug protein per ml in carbonate buffer pH 9.6, 100 ul per well) by incubation for 2 hours at 37° C. followed by overnight incubation at 4° C. Plates were washed between each incubation step using phosphate buffered saline with 0.05% Tween 20 (PBS-T). Plates were then blocked with 2% human serum albumin (ICN, 100 ul/well) in PBS incubated for 1 our at room temperature.

The following BIC preparations were tested: i) C. difficile culture filtrates immune, lot #900918 ("#18") and lot #921019 ("#19"), ii) *C. difficile* toxin A immune, lot #900927 ("#27"), and iii) control, "non-immune" BIC, lot #910311 ("#11"). All BIC samples were diluted in PBS-T (serial halving dilutions) and 100 ul per well of sample was incubated for one hour at 37°C. All assays were performed in triplicate.

Horseradish peroxidase-labeled goat anti-bovine IgG (KPL Laboratories) was used as the secondary antibody (0.2 ug/ml in PBS with 2% human serum albumin) incubated for one hour at 37° C. TMB microwell peroxidase substrate (KPL Laboratories) was used as substrate (100 ul/well) and stopped after 2 to 5 minutes with an equal volume of 1M phosphoric acid. The optical density was then read at 450 nm with 630 nm as reference using an automated photometer (Dynatech). Controls included substitution of the secondary antibody with peroxidase labeled anti-human IgG and omission of the peroxidase substrate solution. Results are expressed at the mean optical density of test wells minus mean optical density of background wells (coated with human serum albumin alone).

Figure 1:
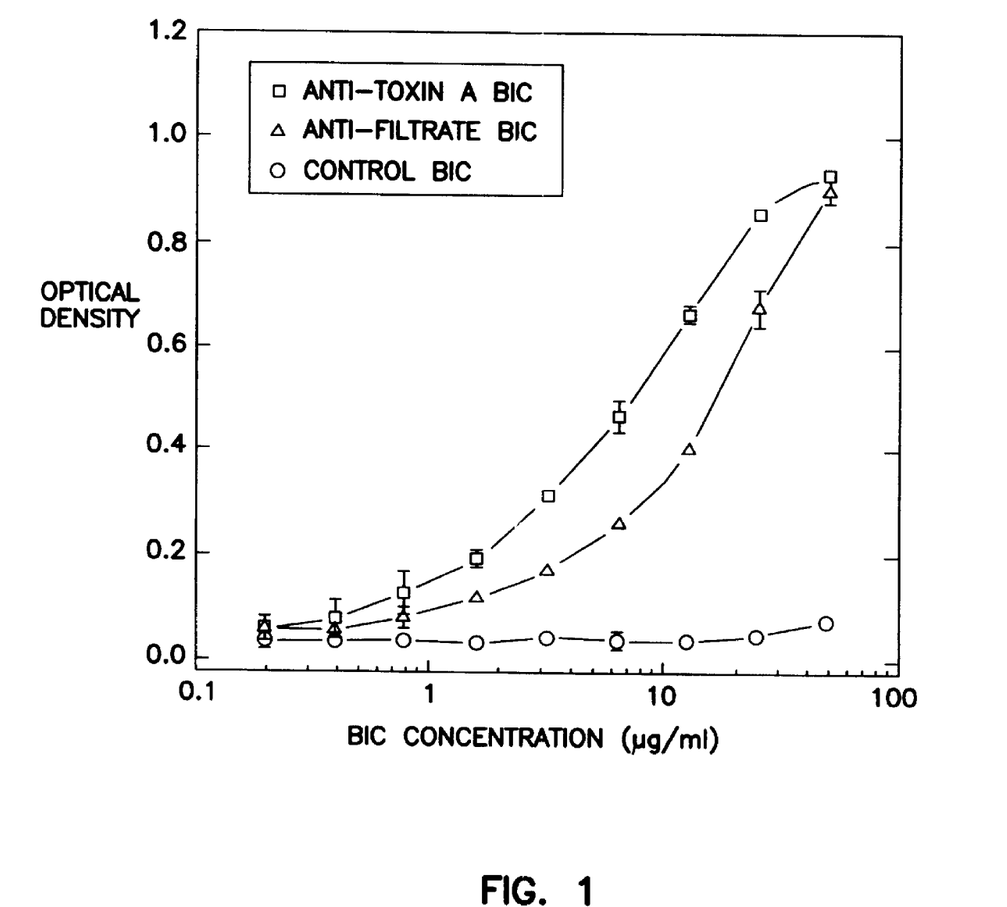
FIG. 1 is a graphic illustration of Anti-*clostridium difficile* Toxin A antibody levels by the ELISA method.
Figure 2:
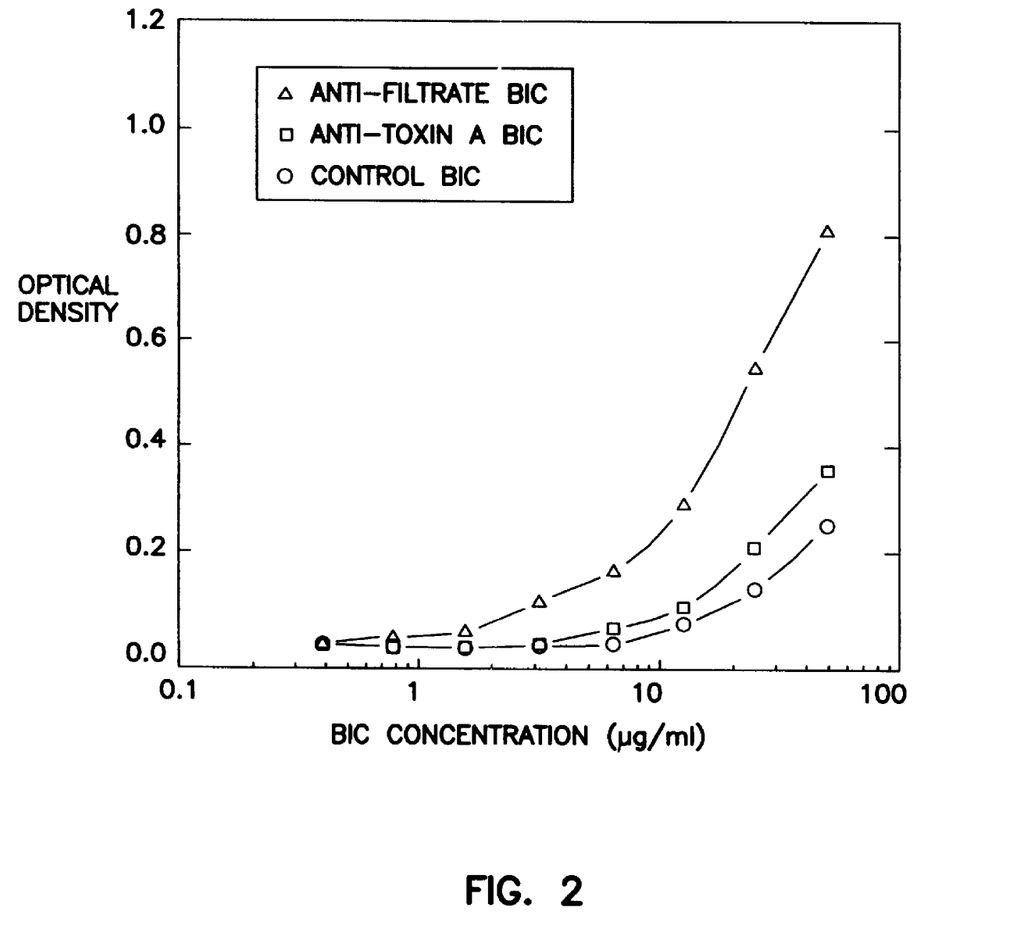
FIG. 2 is a graphic illustration of Anti-*clostridium difficile* Toxin B antibody levels by the ELISA method.

Both the anti-filtrate and the anti-toxin A BIC preparations had substantially higher IgG antibody levels to purified toxin A. In this instance the highest antibody levels were in colostrum from toxin A immunized animals [FIG. 1]. Increased IgG antibody levels to purified toxin B were evident in the anti-filtrate BIC. Anti-toxin A BIC showed a marginal increase in toxin B antibody levels as compared to control when assayed on a weight for weight basis [FIG. 2].
*C. difficile* Whole Cell Bovine Antibody Binding:

Toxigenic intact *C. difficile* were washed to remove extracellular toxins, diluted in pH 9.6 carbonate buffer and incubated overnight at 4° C. in a microtiter plate to 5 bind bacteria to plate. Bovine Immunoglobulin Concentrate (BIC powder, nonimmune and immune to *C. difficile* antigens, was incubated with the bound intact *C. difficile*. Affinity purified, peroxidase-labeled goat antibody to bovine immunoglobulin (heavy and light chain) and tetramethylbenzidine substrate was used to detect the quantity of bovine immunoglobulin bound to the intact *C. difficile*. Antibody binding was quantitated by reading the absorbance at 480 nm of the wells in the microtiter plate.
Results:

*C. difficile* toxin A immune BIC lot #900927 has eight time more specific antibody activity to whole cell toxigenic *C. difficile* than nonimmune BIC lot #910311.

*C. difficile* culture filtrate immune BIC lot #921019 has four to eight time more specific antibody activity to whole cell toxigenic *C. difficile* than nonimmune BIC lot #910311.

EXAMPLE 3

Bactericidal Activity of Bovine Antibody to *C. difficile*:

Log phase toxigenic *C. difficile* was combined with either BIC powder immune to *C. difficile* toxins or media alone to serve as a 100% growth control. After a four hour incubation at room temperature in an anaerobic chamber, the bacteria+ BIC and the bacteria+media were serially diluted in media and then plated onto tryptic soy blood agar (TSBA) plates. The TSBA plates were incubated for 16 hours at 37° C. in an anaerobic chamber and then individual bacteria colonies were counted.
Results:

*C. difficile* toxin A immune BIC lot #900927 reconstituted at 10% (weight/volume) and further diluted 1:2 (final) kills -90% of *C. difficile* in the reaction culture.

*C. difficile* culture filtrate immune BIC lot #921019 reconstituted at 10% (weight/volume) and further diluted 1:2 (final) kills 90–95% of *C. difficile* in the reaction culture.

See also Table 1.

TABLE 1

Bactericidal Effects of Bovine Immunoglobulin Against Toxigenic *C. difficile*

| Sample | Colonies @ 1:1000 | Colonies @ 1:10,000 |
|---|---|---|
| Bacteria + Media Control | >300 | 203 |
| BIC #921019 @ 1:2 + Bacteria | 4 | 1 |
| Bacteria + Media Control | >300 | 21 |
| BIC #900927 @ 1:2 + Bacteria | 75 | 1 |

EXAMPLE 4

Figure 3:
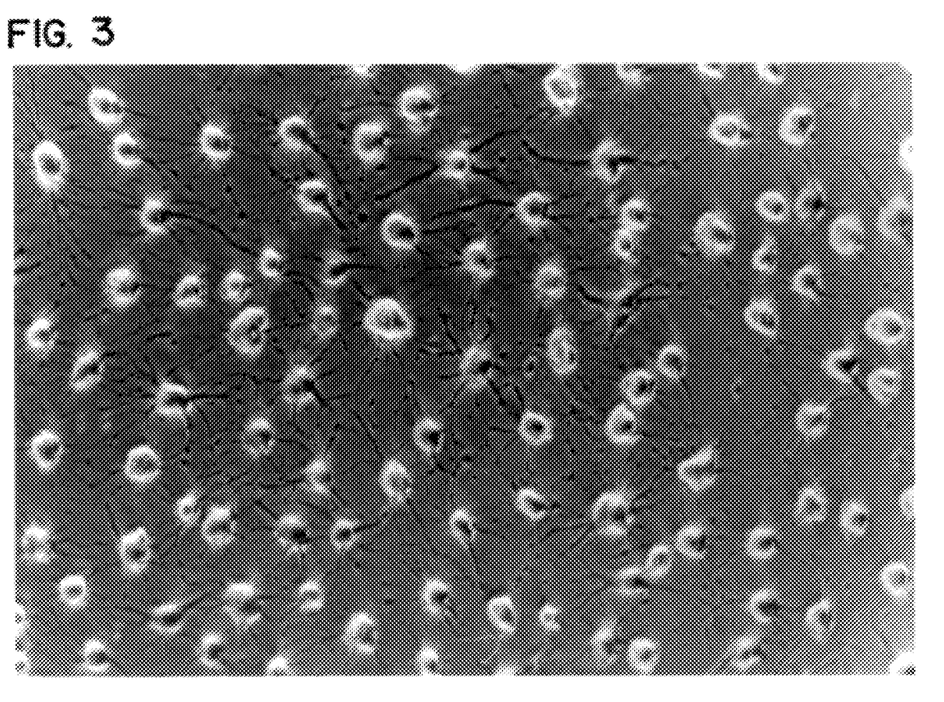
FIG. 3 is a photomicrograph of monolayer of IMR-90 fibroblasts after exposure to *C. difficile* culture filtrate (×10 minimum cytotoxic dose) for 24 hours. There is marked cytopathic effect with rounding of all cells.
Figure 4:
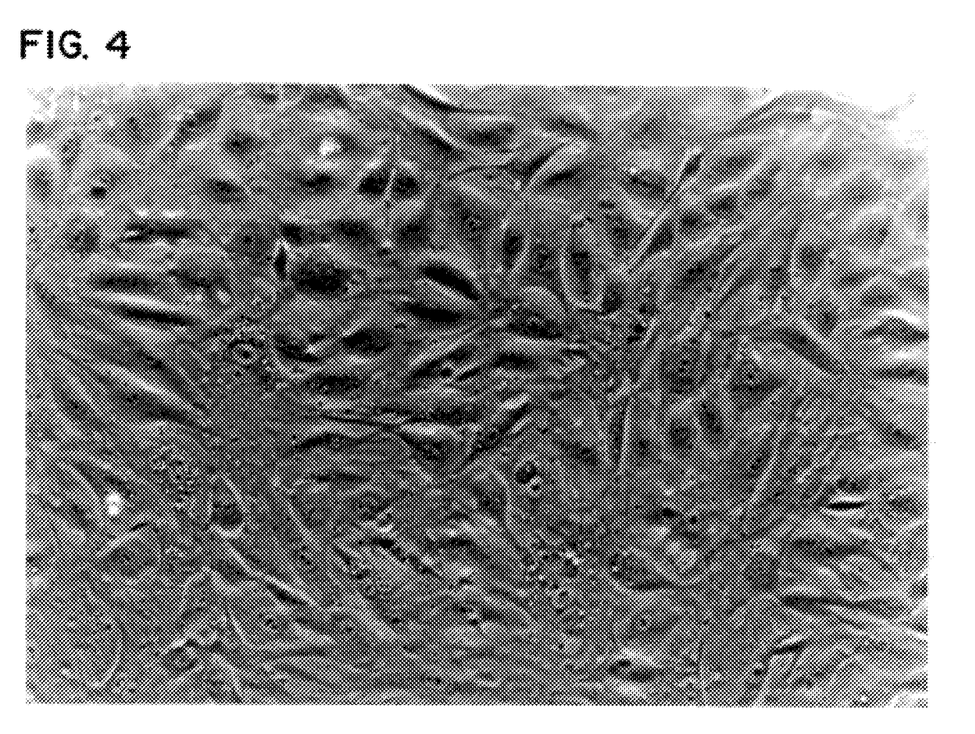
FIG. 4 is a photomicrograph of a monolayer of IMR-90 fibroblasts exposed for 24 hours to *C. difficile* culture filtrate (×10 minimum cytotoxic dose) preincubated with antifiltrate BIC (100 mg/ml). The anti-filtrate BIC effectively inhibited the cytopathic effect and the monolayer demonstrates a normal morphology.

To demonstrate that anti-*C. difficile* BIC is capable of inhibiting the cytotoxic effects of *C. difficile* toxins.
Cytotoxicity Method Cytotoxicity was determined by cell rounding of confluent monolayers of IMR-90 fibroblasts in tissue culture. The cytotoxic effects of *C. difficile* culture filtrate and of purified *C. difficile* toxins A and B were examined. The minimum cytotoxic dose of each preparation was defined as the minimum dose resulting in 100% cell rounding at 24 hours (0.1–1 ng of protein/ml for culture filtrate, 10–25 ng/ml for toxin A and 0.003 ng/ml for toxin B, the ranges representing the varying potency of the different toxin preparations used in these studies). The neutralizing activity of the various BIC preparations were quantified by adding halving dilutions of BIC to either the minimum cytotoxic dose of each toxin preparation or to 10 times the minimum cytotoxic dose and assessing cell rounding after 24 hours. In each instance results are expressed as the lowest concentration of BIC required to prevent rounding of >50% of the IMR-90 cells.
Results:

Results for the cytotoxicity inhibition experiments are summarized in Tables 2 & 3. FIG. 3 is a photomicrograph of an IMR-90 monolayer which had been exposed to ×10 the minimum cytotoxic dose of *C. difficile* culture filtrate for 24 hours. All cells demonstrate cell rounding typical of the cytopathic effects of *C. difficile* toxins. FIG. 4 illustrated a similar IMR-90 monolayer which was also exposed to the same concentration of *C. difficile* filtrate. In this instance, however, the filtrate was incubated for 1 hour at room temperature with anti-*C. difficile* BIC (#18, 100 ug/ml) prior to its addition to the monolayer. The anti-*C. difficile* filtrate BIC effectively prevented the cytotoxic effects of *C. difficile* toxins.

TABLE 2

(circa ×10 Minimum Cytotoxic Dose)

| BIC Preparation | Culture Filtrate (10 ng/ml) | Toxin A (250 ng/ml) | Toxin B (0.03 ng/ml) |
|---|---|---|---|
| Anti-Filtrate (#18) | 6 ug/ml | 1 mg/ml | 8 ug/ml |
| Anti-Toxin A (#27) | >1 mg/ml | >1 mg/ml | >1 mg/nl |
| Control BIC (#11) | >1 mg/ml | >1 mg/ml | >1 mg/ml |

TABLE 3

(circa ×1 Minimum Cytotoxic Dose)

| BIC Preparation | Culture Filtrate (0.1 ng/ml) | Toxin A (10 ng/ml) | Toxin B (0.003 ng/ml) |
|---|---|---|---|
| Anti-Filtrate (#18) | 0.02 ug/ml | 60 ug/ml | <0.5 ug/ml |
| Anti-Toxin A (#27) | 12 ug/ml | 500 ug/ml | 8 ug/ml |
| Control BIC (#11) | 25 ug/ml | >1 mg/ml | 31 ug/ml |

Anti-*C. difficile* culture filtrate BIC (#18) effectively blocked the cytotoxic effects of *C. difficile* culture filtrate and of purified toxin A and toxin B.

Anti-toxin A BIC (#27) was less effective in inhibiting cytotoxicity.

EXAMPLE 5

To demonstrate that anti-*C. difficile* BIC is capable of blocking the binding of *C. difficile* toxin A to its enterocyte brush border receptor.

Method Purified *C. difficile* toxin A was $^3$H-labelled using a modified Bolton-Hunter protocol as previously described (C. Pothoulakis et al., *J. Clin. Invest.* 1991; 88:119–125). Radiolabelled toxin A migrates identically to native toxin on both SDS-PAGE and HPLC and retains full biological activity as a cytotoxin (IMR-90 fibroblast rounding assay) and enterotoxin (rabbit ileal loop assay). In earlier studies using $^3$H-toxin A, the presence of a single class of toxin A receptors on rabbit ileal brush border with a $K_d$ of $5.4 \times 10^{-8}$ M and a maximum binding capacity of 5.9 pmol toxin A/mg brush border protein was demonstrated. Brush border membranes (BBM) were purified, from rabbit ileum by EDTA-chelation as previously described in the above reference. The purity of the BBM was determined by light microscopy and by measurement of alkaline phosphatase and sucrase activity.

Toxin A-BBM binding experiments were performed in triplicate in 1.8 ml Eppendorf tubes precoated with 5% skim milk in 50 mM Tris, 0.2M NaCl (pH 7.4). Anti-*C. difficile* BIC (30 μl) at varying concentrations was incubated with 200 ng of $^3$H-toxin A (approximately 35,000 dpm/pmol specific activity) in 145 μl 50 mM Tris (pH 7.4) for 2 hours at 20° C. The samples were then cooled to 4° C. and 200 μg of purified BBM in 25 ul of 50 mM Tris was added. Following a one hour incubation at 4° C. 1 ml of 50 mM Tris buffer was added and the tubes centrifuged for 4 min at 11,000 g. The BBM pellets were washed twice with 1 ml of 50 mM Tris and then dissolved in 0.4 ml of buffer containing 10% SDS. Membrane associated radioactivity was measured by liquid scintillation counting. Results are expressed as specific toxin A binding. Specific binding being defined as total $^3$H-toxin A bound minus $^3$H-toxin A bound in the presence of 100 fold excess native, unlabelled, toxin A.

Results

Figure 5:
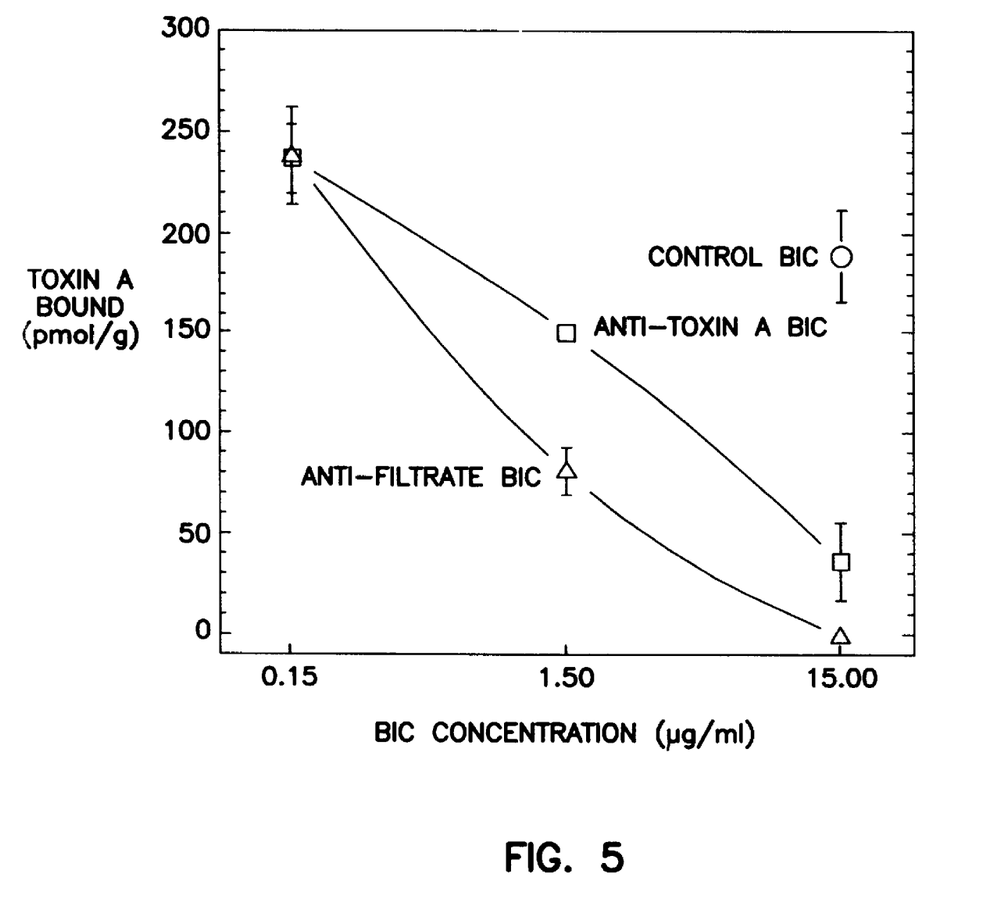
FIG. 5 is a graphic illustration of Anti-*clostridium difficile* BIC inhibiting binding of Toxin A to its enterocyte receptor.

Results are illustrated in FIG. 5 (expressed as mean±SE). Specific toxin A binding is expressed as pmol of $^3$H-toxin A bound per gram of brush border membrane protein (pmol/g).

Anti-filtrate BIC (#18) inhibited the specific binding of $^3$H-toxin to brush border membrane in a dose-dependent fashion. At a concentration of 15 ug/ml the anti-filtrate BIC completely blocked toxin A-receptor binding. The anti-toxin A BIC also substantially reduced toxin A binding in a dose-dependent manner. At a concentration of 15 ug/ml the anti-toxin A BIC blocked toxin A-receptor binding by 84% in comparison with the same concentration of control, non-immune BIC.

Bovine immunoglobulin concentrate from cows immunized against *C. difficile* culture filtrate or *C. difficile* toxin A are capable of reducing the specific binding of toxin A to purified rabbit brush border membrane. Inhibition of toxin A-receptor binding presumably results from binding of bovine IgG anti-toxin to toxin A thereby blocking subsequent toxin-receptor interaction. This represents a putative mechanism of action for the protective effects of anti-*C. difficile* BIC in inhibiting the enterotoxic effects of toxin A in vivo.

EXAMPLE 6

To demonstrate that anti-*C. difficile* BIC is capable of inhibiting the enterotoxic effects of *C. difficile* toxins.

Enterotoxicity Method

Fasting male Wister rats were anesthetized by intraperitoneal injection of sodium pentobarbital. Laparotomy was performed, the renal pedicles tied and 3H-mannitol (10 uCi, NEN, Boston, Mass.) administered intravenously. Closed ileal loops (5 cm) were then formed and injected with 400 ul of 50 mM Tris buffer (pH 7.4) or with Tris buffer containing *C. difficile* culture filtrate (20 ug of protein). The inhibitory effect of anti-*C. difficile* BIC was assessed by the addition of BIC (200 ug) to the toxins prior to injection into the ileal lumen. The following BIC preparations were tested: i) *C. difficile* culture filtrate immune (#18 and #19), ii) *C. difficile* toxin A immune (#27), and iii) control non-immune BIC (#11).

The abdominal incision was closed and anaesthesia maintained with sodium pentobarbital. The animals were sacrificed after 4 hours and the ileal loops immediately harvested. Loop weight to length ratio was determined as a measure of enterotoxin effect. Mannitol excretion, indicating intestinal permeability, was measured by counting radioactivity in the luminal fluid. Ileal tissue samples were also fixed in formalin, paraffin-embedded and sections stained with hematoxylin and eosin. The histologic severity of enteritis was graded taking into account the following features: i) neutrophil margination and tissue infiltration, ii) hemorrhagic congestion and edema of the mucosa, iii) epithelial cell damage. A score of 0 to 3, denoting increasingly severe abnormality, as assigned to each of these parameters by a blinded, histopathologist.

Results

Figure 6:
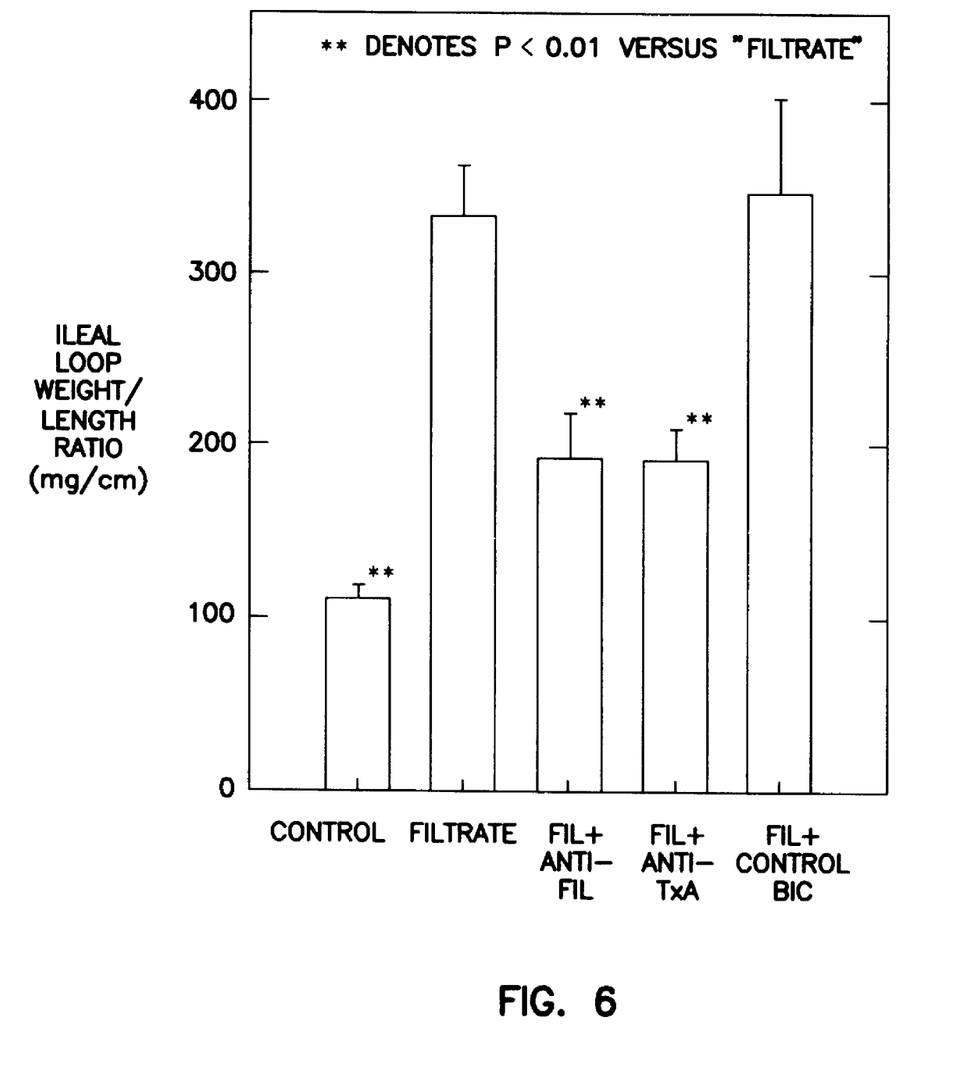
FIG. 6 is a graphic block illustration showing the 30 effect of Bovine Immunoglobulin Concentrate (BIC) on *Clostridium difficile* culture filtrate induced fluid secretion in rat ileal loops.
Figure 7:
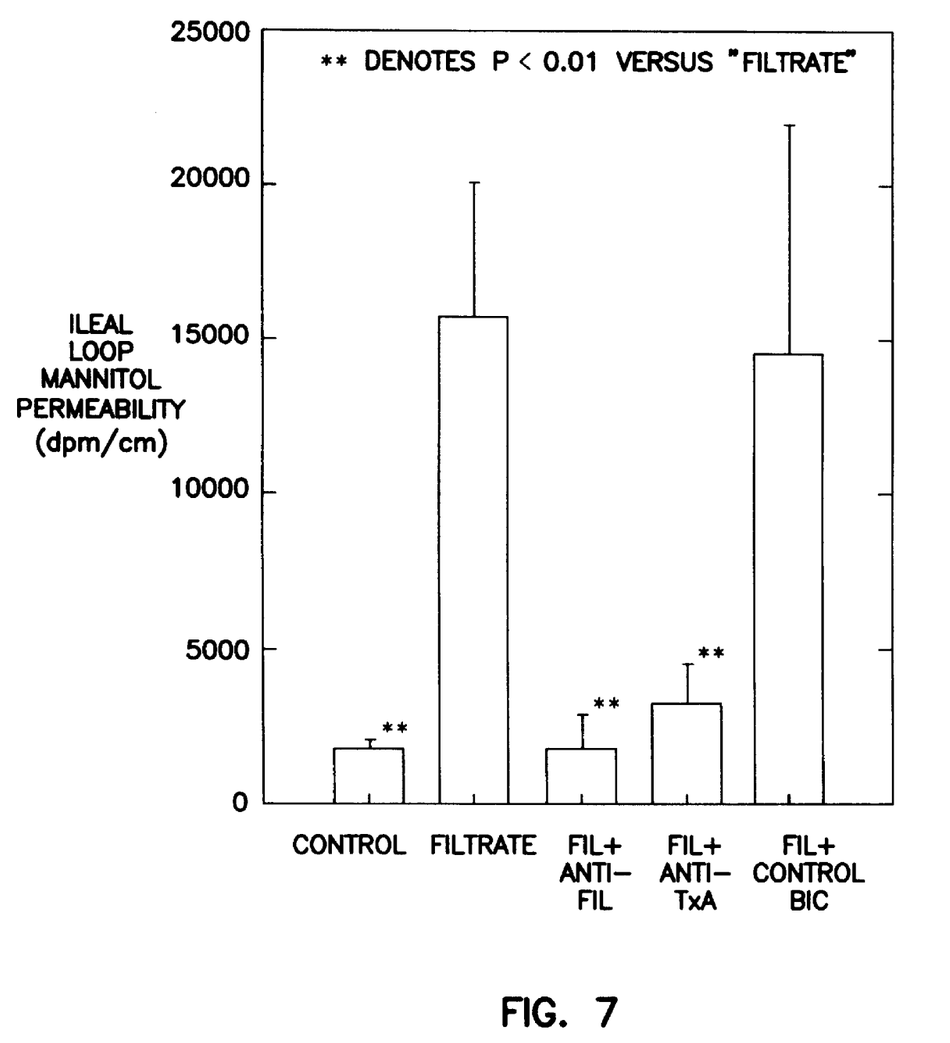
FIG. 7 is a graphic block illustration showing the effect of BIC on *C. difficile* culture filtrate induced mannitol permeability in rat ileal loops.

As expected *C. difficile* culture filtrate showed enterotoxic effects as evidenced by substantial increases in weight to length ratio [FIG. 6] and mannitol excretion [FIG. 7] in filtrate exposed ileal loops. *C. difficile* culture filtrate immune BIC (Anti-Fil) substantially inhibited these enterotoxic effects (by 54% for weight/length ration [FIG. 6] and by 100% for mannitol permeability [FIG. 7], P<0.01 for both). *C. difficile* toxin A immune BIC (Anti-TxA) effected a similar inhibition of filtrate-induced enterotoxicity (64% for weight/length ration [FIG. 6] and 89% for mannitol permeability [FIG. 7], P<0.01 for both). Control, non-immune BIC did not inhibit had no significant effect on the enterotoxicity of the culture.

Figure 8:
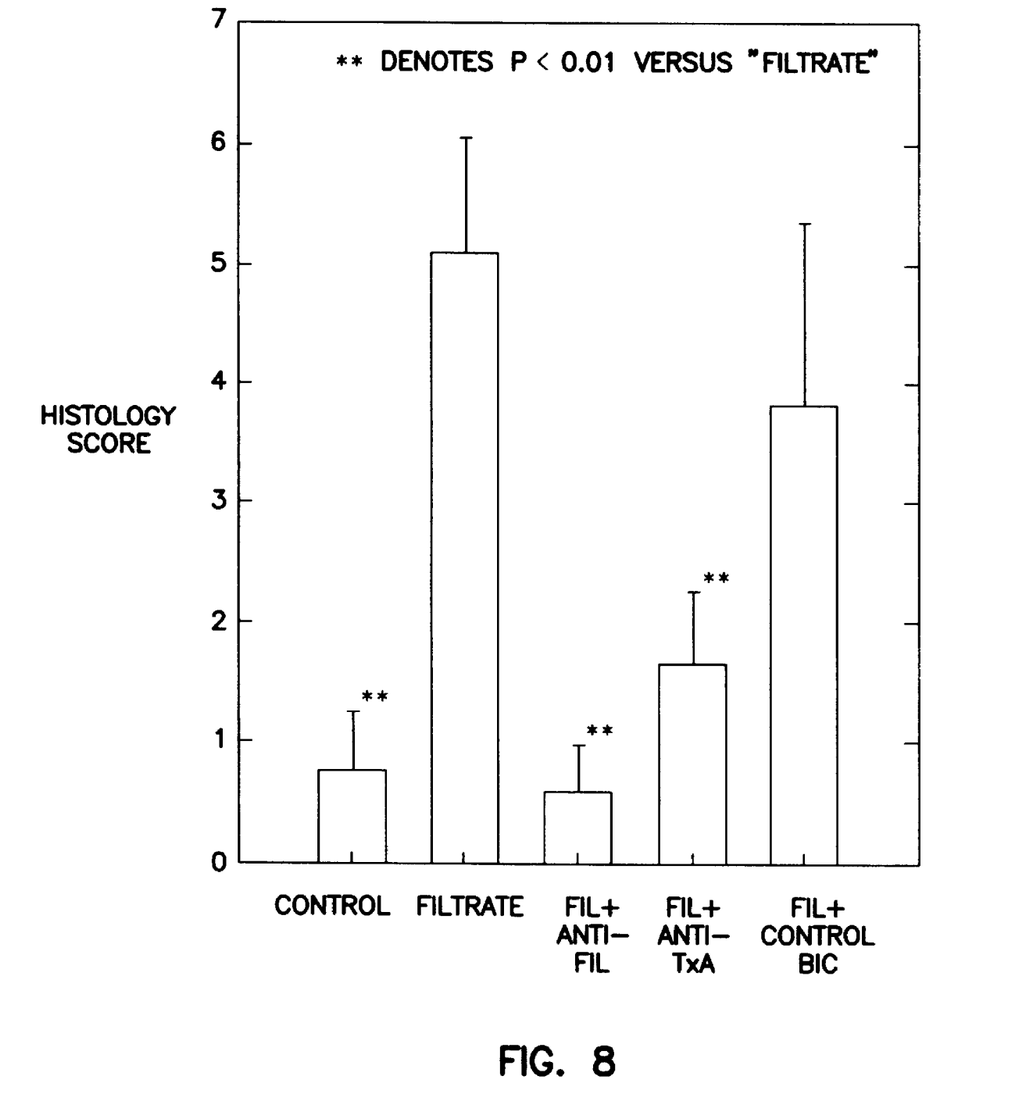
FIG. 8 is a graphic block illustration showing effect of BIC on *C. difficile* culture filtrate induced enteritis in rat ileal loops.

Histologic examination of ileal loop tissue showed significant damage, reflected as an increase in Histology Score, in tissues exposed to *C. difficile* culture filtrate [FIG. 8]. Anti-filtrate BIC and anti-toxin A BIC both significantly attentuated the enteritis induced by the *C. difficile* filtrate as evidenced by a substantial lowering of Histology Scores. The control, non-immune, BIC had no significant protective effect.

Figure 9:
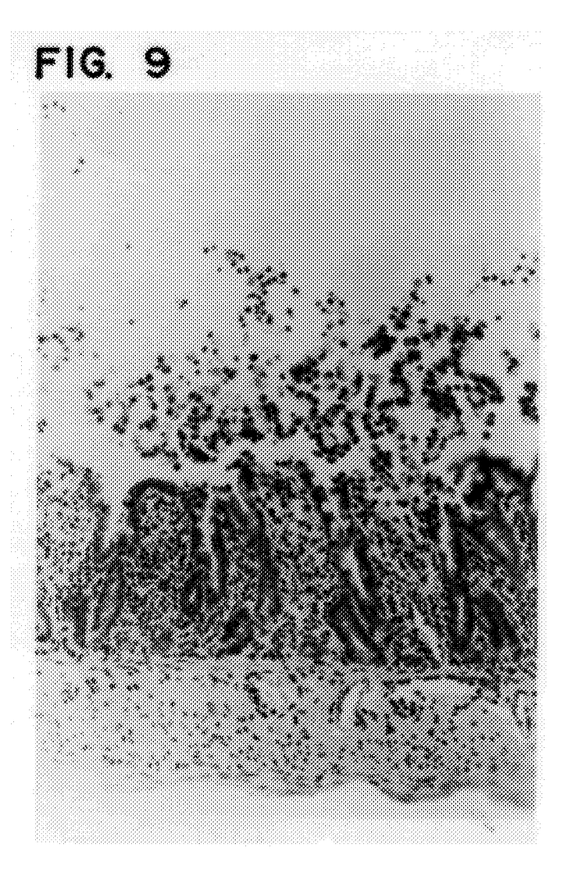
FIG. 9 is a photomicrograph of ileal tissue exposed to *C. difficile* culture filtrate.
Figure 10:
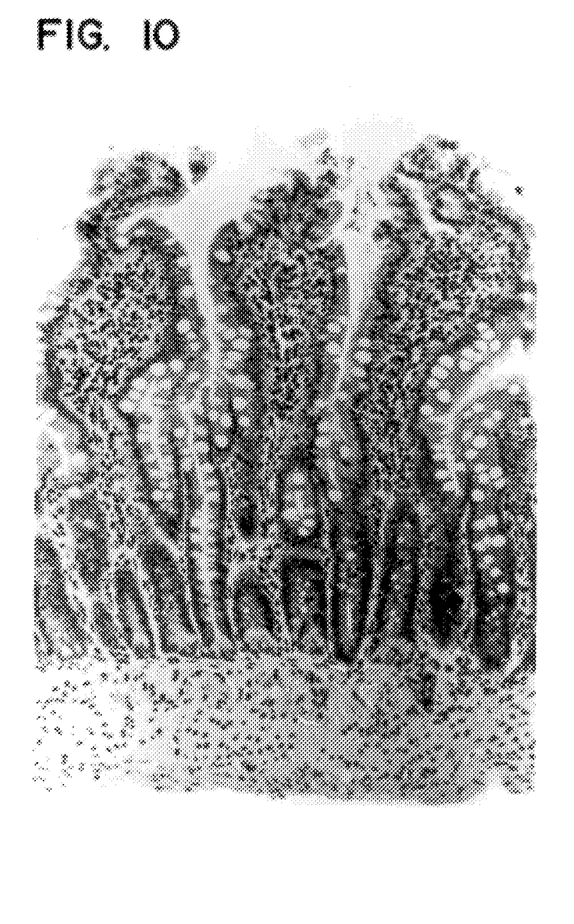
FIG. 10 is a photomicrograph of ileal tissue exposed to *C. difficile* culture filtrate preincubated with anti-*C. difficile* filtrate BIC.

FIG. 9 is a photomicrograph illustrating a representative section of ileal mucosa after exposure to *C. difficile* culture filtrate. There is complete destruction of normal villous architecture. Vascular congestion (vessels at bottom center and right) as well as neutrophil margination and tissue infiltration are evident. FIG. 10 illustrates the protective effect of anti-filtrate BIC. The architecture is preserved apart from mild disruption and edema of the villous tips. There is minimal inflammatory infiltrate or congestion of the submucosal vessels.

*C. difficile* culture filtrate immune BIC substantially inhibits filtrate-induced enterotoxicity in rat ileum. A similar degree of inhibition is seen in *C. difficile* toxin A immune BIC. These data are consistent with our previous findings that *C. difficile* toxin-induced enterotoxicity in rodent intestine is mediated by toxin A. Toxin B has no demonstrable enterotoxic effects in this animal model, although toxins A and B may act synergistically to produce disease symptoms in humans.

What is claimed is:

1. A method of treating pseudomembranous colitis in a human comprising: administering, in a tablet, capsule or suppository, to said human suffering therefrom an amount of anti-*Clostridium difficile* bovine immunoglobulin concentrate effective for treating said colitis.

2. The method of claim 1 where the tablet or capsule is enteric coated.

3. The method of claim 1, wherein the bovine immunoglobulin concentrate is microencapsulated.

4. A method of treating antibiotic associated diarrhea in a human comprising: administering, in a tablet or capsule, to said human suffering therefrom an amount of anti-*Clostridium difficile* bovine immunoglobulin concentrate effective for treating said diarrhea.

5. The method of claim 4, wherein the tablet or capsule is enteric coated.

6. A method of treating pseudomembranous colitis or antibiotic associated diarrhea in a human comprising administering to said human suffering therefrom:

(a) an amount of anti-*Clostridium difficile* bovine immunoglobulin concentrate concurrently or following the administration of;

(b) an amount of vancomycin, bacitracin or metronidazole; both amounts of (a) and (b) effective for treating said colitis or antibiotic associated diarrhea.

* * * * *